US008598079B2

(12) United States Patent
Hungenberg et al.

(10) Patent No.: US 8,598,079 B2
(45) Date of Patent: Dec. 3, 2013

(54) ACTIVE COMPOUND COMBINATIONS

(75) Inventors: Heike Hungenberg, Langenfeld (DE); Anne Suty-Heinze, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 71 days.

(21) Appl. No.: 13/173,195

(22) Filed: Jun. 30, 2011

(65) Prior Publication Data

US 2012/0004100 A1 Jan. 5, 2012

Related U.S. Application Data

(60) Provisional application No. 61/360,077, filed on Jun. 30, 2010.

(30) Foreign Application Priority Data

Jun. 30, 2010 (EP) .................................... 10167887

(51) Int. Cl.

*A01N 43/56* (2006.01)
*A01P 3/00* (2006.01)
*A01P 7/02* (2006.01)
*A01P 7/04* (2006.01)

(52) U.S. Cl.

USPC ............................ 504/100; 514/406; 514/341

(58) Field of Classification Search

USPC ........................... 514/341, 357, 406; 504/100

See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,808,430 | A | 2/1989 | Kouno |
| 5,876,739 | A | 3/1999 | Turnblad et al. |
| 2003/0176428 | A1 | 9/2003 | Schneidersmann et al. |
| 2004/0204470 | A1 | 10/2004 | Elbe et al. |
| 2007/0299264 | A1 | 12/2007 | Huang et al. |
| 2008/0293566 | A1 | 11/2008 | Suty-Heinze et al. |
| 2010/0022389 | A1 | 1/2010 | Langewald et al. |
| 2010/0028304 | A1 | 2/2010 | Koyanagi et al. |
| 2010/0063007 | A1 | 3/2010 | Hungenberg et al. |
| 2011/0160061 | A1 | 6/2011 | Jeschke et al. |

FOREIGN PATENT DOCUMENTS

| | | | |
|---|---|---|---|
| DE | 10 2006 037 120 | A1 | 9/2007 |
| WO | WO 02/28186 | A2 | 4/2002 |
| WO | WO 02/080675 | A1 | 10/2002 |
| WO | WO 2006/108552 | A2 | 10/2006 |
| WO | WO 2007/095229 | A2 | 8/2007 |
| WO | WO 2007/149134 | A1 | 12/2007 |
| WO | WO 2008/077930 | A2 | 7/2008 |
| WO | WO 2009/062905 | A1 | 5/2009 |
| WO | WO 2009/124707 | A2 | 10/2009 |
| WO | WO 2010/000790 | A1 | 1/2010 |
| WO | WO 2010/040623 | A1 | 4/2010 |

OTHER PUBLICATIONS

Bauer, T.A., et al., "Response of Selected Weed Species to Postemergence Imazethapyr and Bentazon," *Weed Tech*. 9:236-242, The Weed Science Society of America, United States (1995).

Blackshaw, R.E., "HOE-39866 Use in Chemical Fallow Systems," *Weed Tech*. 3:420-428, The Weed Science Society of America, United States (1989).

Blackshaw, R.E., "Synergistic Mixes of DPX-A7881 and Clopyralid in Canola (*Brassica napus*)," *Weed Tech*. 3:690-695, The Weed Science Society of America, United States (1989).

Blackshaw, R.E., et al., "Herbicide Combinations for Postemergent Weed Control in Safflower (*Carthamus tinctorius*)," *Weed Tech*. 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech*. 18:464-472, The Weed Science Society of America, United States (2004).

Bradley, P.R., et al., "Response of Sorghum (*Sorghum bicolor*) to Atrazine, Ammonium Sulfate, and Glyphosate," *Weed Tech*. 14:15-18, The Weed Science Society of America, United States (2000).

Buker, III, R.S., et al., "Confirmation and Control of a Paraquat-Tolerant Goosegrass (*Eleusine indica*) Biotype," *Weed Tech*. 16:309-313, The Weed Science Society of America, United States (2002).

Burke, I.C., et al., "CGA-362622 Antagonizes Annual Grass Control with Clethodim," *Weed Tech*. 16:749-754, The Weed Science Society of America, United States (2002).

Colby, S.R., "Calculating Synergistic and Antagonistic Responses of Herbicide Combinations," *Weeds 15*:20-22, Weed Society of America, United States (1967).

Flint, J.L., et al., "Analyzing Herbicide Interactions: A Statistical Treatment of Colby's Method," *Weed Tech*. 2:304-309, The Weed Science Society of America, United States (1988).

Gillespie, G.R. and Nalewaja, J.D., "Wheat (*Triticum aestivum*) Response to Triallate Plus Chlorsulfuron," *Weed Tech*. 3:20-23, The Weed Science Society of America, United States (1989).

Green, J.M., et al., "Metribuzin and Chlorimuron Mixtures for Preemergence Broadleaf Weed Control in Soybeans, *Glycine max,*" *Weed Tech*. 2:355-363, The Weed Science Society of America, United States (1988).

Harker, K.N. and O'Sullivan, A., "Synergistic Mixtures of Sethoxydim and Fluazifop on Annual Grass Weeds," *Weed Tech*. 5:310-316, The Weed Science Society of America, United States (1991).

Kent, L.M., et al., "Effect of Ammonium Sulfate, Imazapyr, and Environment on the Phytotoxicity of Imazethapyr," *Weed Tech*. 5:202-205, The Weed Science Society of America, United States (1991).

Kotoula-Syka, E., et al., "Interactions Between SAN 582H and Selected Safeners on Grain Sorghum (*Sorghum bicolor*) and Corn (*Zea mays*)," *Weed Tech*. 10:299-304, The Weed Science Society of America, United States (1996).

(Continued)

*Primary Examiner* — John Pak

(74) *Attorney, Agent, or Firm* — Sterne, Kessler, Goldstein & Fox P.L.L.C.

(57) ABSTRACT

The present invention relates to novel active compound combinations consisting of, firstly, the known carboxamide penflufen and, secondly, known insecticidally active compounds, which combinations are highly suitable for controlling unwanted animal pests such as insects or acarids and also unwanted phytopathogenic fungi.

11 Claims, No Drawings

(56) References Cited

OTHER PUBLICATIONS

Lanclos, D.Y., et al., "Glufosinate Tank-Mix Combinations in Glufosinate-Resistant Rice (*Oryza satiya*)," *Weed Tech.* 16:659-663, The Weed Science Society of America, United States (2002).
Norris, J.L., et al., "Weed Control from Herbicide Combinations with Three Formulations of Glyphosate," *Weed Tech.* 15:552-558, The Weed Science Society of America, United States (2001).
Novosel, K.M., et al., "Metolachlor Efficacy as Influenced by Three Acetolactate Synthase-Inhibiting Herbicides," *Weed Tech.* 12:248-253, The Weed Science Society of America, United States (1998).
Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).
Rummens, F.H.A., "An Improved Definition of Synergistic and Antagonistic Effects," *Weed Science* 23:4-6, The Weed Science Society of America, United States (1975).
Salzman, F.P. and Renner, K.A., "Response of Soybean to Combinations of Clomazone, Metribuxin, Linuron, Alachlor, and Arazine," *Weed Tech.* 6: 922-929, The Weed Science Society of America, United States (1992).
Scott, R.C., et al., "Spray Adjuvant, Formulation, and Environment Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).
Shaw, D.R. and Arnold, J.C., "Weed Control from Herbicide Combinations with Glyphosate," *Weed Tech.* 16:1-6, The Weed Science Society of America, United States (2002).
Snipes, C. and Allen, R.L., "Interction fo Graminicides Applied in Combination with Pyrithiobac," *Weed Tech.* 10:889-892, The Weed Science Society of America, United States (1996).
Sun, Y.-P., et al., "Analysis of Joint Action of Insecticides Against House Flies," *J. Econ. Entomol.* 53:887-892, Entomological Society of America, United States (1960).
Tammes, P.M.L., "Isoboles, A Graphic Representation of Synergism in Pesticides," *Neth. J. Plant Path.* 70:73-80, Springer, Germany (1964).
Tomlin, C.D.S., "Chlorantraniliprole," in *The Pesticide Manual*, 15th Edition, p. 175-176, Tomlin, C.D.S., ed., British Crop Protection Council (BCPC) Publications, Hampshire, United Kingdom (2009).
Wehtje, G., and Walker, R.H., "Interaction of Glyphosate and 2,4-DB for the Control of Selected Morningglory (*Ipomoea* spp.) Species," *Weed Tech.* 11:152-156, The Weed Science of America, United States (1997).
Yu, H., et al., "Snthesis and insecticidal activity of *N*-cyano 2-(substituted amino) ethyl methyl sulfoximine derivatives," *ARKIVOC 16*:99-109, ARKAT USA, Inc., United States (2008).
Zhang, W., et al., "Fenoxaprop Interactions for Barnyardgrass (*Echinochloa crus-galli*) Control in Rice," *Weed Tech.* 19: 293-297, The Weed Science Society of America, United States (2005).
Unverified English language abstract of German Patent Publication No. DE 10 2006 037 120 A1, European Patent Office, espacenet database—Worldwide (2007).

ACTIVE COMPOUND COMBINATIONS

The present invention relates to novel active compound combinations consisting of, firstly, the known carboxamide penflufen and, secondly, known insecticidally active compounds, which combinations are highly suitable for controlling unwanted animal pests such as insects or acarids and also unwanted phytopathogenic fungi.

It is already known that the carboxamide N-[2-(1,3-dimethylbutyl)phenyl]-5-fluoro-1,3-dimethyl-1H-pyrazole-4-carboxamide (penflufen) has fungicidal properties: for example from WO 03/010149. The activity of this compound is good; however, at low application rates, it is sometimes unsatisfactory.

Also known are the active compounds Rynaxypyr (chlorantraniliprole) and sulfoxaflor, Rynaxypyr (chlorantraniliprole) for example from "The Pesticide Manual", Tomlin C. D. S. (Ed.), Vol. 15, BCPC, pages 175-176 and sulfoxaflor from WO 2007/095229 A2 and WO-A-2007/149134.

Also known are mixtures of anthranilamides and carboxamides from WO-A-2006/108552. However, this publication does not mention mixtures of penflufen and Rynaxypyr. WO-A-2006/108552 does not mention penflufen at all.

WO-A-2008/077930 (US-A-2010/0063007) discloses mixtures of fosetyl-Al with insecticides and fungicides, Rynaxypayr being mentioned as one possibility from among a large number of insecticides and penflufen being mentioned as one possibility from among a large number of fungicides. However, this publication does not specifically disclose a mixture comprising Rynaxypyr and penflufen.

WO-A-2009/124707 discloses mixtures comprising a biological control agent and an insecticide and a fungicide, Rynaxypyr being mentioned as one possibility from among a large number of insecticides and penflufen being mentioned as one possibility from among a large number of fungicides. However, this publication does not specifically disclose the mixture comprising Rynaxypyr and penflufen.

WO-A-2010/022897 discloses mixtures of sulphoximines with an insecticide or a fungicide, sulfoxaflor being mentioned as one possibility from among a large number of sulfoximines and penflufen being mentioned as one possibility from among a large number of fungicides. However, this publication does not specifically disclose the mixture comprising sulfoxaflor and penflufen.

WO-A-2009/062905 discloses mixtures comprising cyanosulphoximines with a fungicide, sulfoxaflor being mentioned as one possibility from among a large number of cyanosulfoximines and penflufen being mentioned as one possibility from among a large number of fungicides. However, this publication does not specifically disclose the mixture comprising sulfoxaflor and penflufen.

The present invention now provides novel active compound combinations having very good fungicidal, insecticidal and/or acaricidal properties comprising (1) the compound of the formula N-[2-(1,3-dimethylbutyl)phenyl]-5-fluoro-1,3-dimethyl-1H-pyrazole-4-carboxamide:

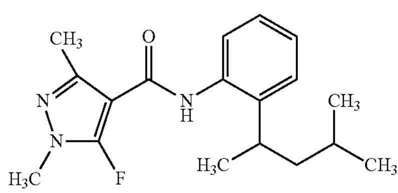 [SMILES: Cc1nn(C)c(F)c1C(=O)Nc1ccccc1C(C)CC(C)C]

(penflufen) known from WO 03/010149 and (2) the compound of the formula 3-bromo-N-[4-chloro-2-methyl-6-(methylcarbamoyl)phenyl]-1-(3-chloropyridin-2-yl)-1H-pyrazole-5-carboxamide:

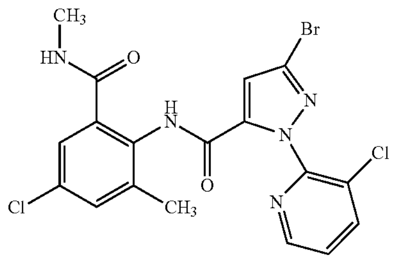 [SMILES: CNC(=O)c1cc(Cl)cc(C)c1NC(=O)c1cc(Br)nn1-c1ncccc1Cl]

(Rynaxypyr/chlorantraniliprole), known from "The Pesticide Manual", Tomlin C. D. S. (Ed.), Vol. 15, BCPC, pages 175-176 and/or (3) the compound of the formula [6-trifluoromethylpyridin-3-yl]ethyl](methyl)oxido-$\lambda^4$-sulphanylidene-cyanamide:

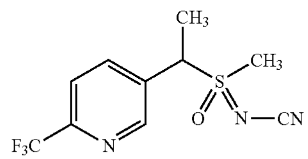 [SMILES: CC(c1ccc(C(F)(F)F)nc1)S(C)(=O)=NC#N]

(sulfoxaflor) known from WO 2007/095229 A2 and WO 2007/149134 A 1

Surprisingly, the fungicidal, insecticidal and/or acaricidal activity of the active compound combination according to the invention is considerably higher than the sum of the activities of the individual active compounds. Accordingly, an unforeseeable synergistic effect is present, and not just an addition of activities.

In addition to the carboxamide N-[2-(1,3-dimethylbutyl)phenyl]-5-fluoro-1,3-dimethyl-1H-pyrazole-4-carboxamide the active compound combinations according to the invention comprise at least one active compound selected from groups (2) and (3).

Emphasis is given in particular to the following active compound combinations according to the invention: penflufen and Rynaxypyr, penflufen and sulfoxaflor and also penflufen and Rynaxypyr and sulfoxaflor.

In addition, the active compound combinations may also comprise further fungicidally, acaricidally or insecticidally active added components.

Preference is also given to the active compound combination which, in addition to penflufen and Rynaxypyr, also comprises the two further active compounds isotianil and imidacloprid.

If the active compounds in the active compound combinations according to the invention are present in certain weight ratios, the synergistic effect is particularly pronounced. However, the weight ratios of the active compounds in the active compound combinations can be varied within a relatively wide range.

In general, the combinations according to the invention comprise penflufen and the mixing partner (2) and/or (3) in the preferred mixing ratios stated in the table below, the mixing ratios being based on ratios by weight.

The ratio is to be understood as the weight ratio of the active compound penflufen (group 1) mixing partner.

TABLE 2

| Mixing ratios | | |
|---|---|---|
| Mixing partner | Preferred mixing ratio | Particularly preferred mixing ratio |
| (2) Rynaxypyr | 50:1 to 1:50 | 10:1 to 1:10 |
| (3) Sulfoxaflor | 50:1 to 1:50 | 10:1 to 1:10 |

The active compound combinations according to the invention have a strong microbicidal action and can be used for controlling unwanted microorganisms; such as fungi and bacteria, in crop protection and in the protection of materials.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Diseases caused by powdery mildew pathogens, such as, for example,

*Blumeria* species, such as, for example, *Blumeria graminis;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;*

Diseases caused by rust disease pathogens, such as, for example,

*Gymnosporangium* species, such as, for example, *Gymnosporangium sabinae*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;*

Diseases caused by pathogens from the group of the Oomycetes, such as, for example,

*Albugo* species, such as, for example, *Albugo candida;*

*Bremia* species, such as, for example, *Bremia lactucae;*

*Peronospora* species, such as, for example, *Peronospora pisi* or *P. brassicae;*

*Phytophthora* species, such as, for example *Phytophthora infestans;*

*Plasmopara* species, such as, for example, *Plasmopara viticola;*

*Pseudoperonospora* species, such as, for example, *Pseudoperonospora humuli* or *Pseudoperonospora cubensis;*

*Pythium* species, such as, for example, *Pythium ultimum;*

Leaf blotch diseases and leaf wilt diseases caused, for example, by

*Alternaria* species, such as, for example, *Alternaria solani;*

*Cercospora* species, such as, for example, *Cereospora beticola;*

*Cladiosporium* species, such as, for example, *Cladiosporium cucumerinum;*

*Cochliobolus* species, such as, for example, *Cochliobolus sativus* (conidia form: *Drechslera*, Syn: *Helminthosporium*) or *Cochliobolus miyabeanus;*

*Colletotrichum* species, such as, for example, *Colletotrichum lindemuthanium;*

*Cycloconium* species, such as, for example, *Cycloconium oleaginum;*

*Diaporthe* species, such as, for example, *Diaporthe citri;*

*Elsinoe* species, such as, for example, *Elsinoe fawcettii;*

*Gloeosporium* species, such as, for example, *Gloeosporium laeticolor;*

*Glomerella* species, such as, for example, *Glomerella cingulata;*

*Guignardia* species, such as, for example, *Guignardia bidwelli;*

*Leptosphaeria* species, such as, for example, *Leptosphaeria maculans* or *Leptosphaeria nodorum;*

*Magnaporthe* species, such as, for example, *Magnaporthe grisea;*

*Mycosphaerella* species, such as, for example, *Mycosphaerelle graminicola, Mycosphaerella arachidicola* or *Mycosphaerella fijiensis;*

*Phaeosphaeria* species, such as, for example, *Phaeosphaeria nodorum;*

*Pyrenophora* species, such as, for example, *Pyrenophora teres* or *Pyrenophora tritici repentis;*

*Ramularia* species, such as, for example, *Ramularia collocygni* or *Ramularia areola;*

*Rhynchosporium* species, such as, for example, *Rhynchosporium secalis;*

*Septoria* species, such as, for example, *Septoria apii* or *Septoria lycopersici;*

*Typhula* species, such as, for example, *Typhula incarnata;*

*Venturia* species, such as, for example, *Venturia inaequalis;*

Root and stem diseases caused, for example, by

*Corticium* species, such as, for example, *Corticium gramirearum;*

*Fusarium* species, such as, for example, *Fusarium oxysporum;*

*Gaeumannomyces* species, such as, for example, *Gaeumannomyces graminis;*

*Plasmodiophora* species, such as, for example, *Plasmodiophora brassicae;*

*Rhizoctonia* species, such as, for example *Rhizoctonia solani;*

*Sarocladium* species, such as, for example, *Sarocladium oryzae;*

*Sclerotium* species, such as, for example, *Sclerotium oryzae;*

*Tapesia* species, such as, for example, *Tapesia acuformis;*

*Thielaviopsis* species, such as, for example, *Thielaviopsis basicola;*

Ear and panicle diseases (including maize cobs) caused, for example, by

*Alternaria* species, such as, for example, *Alternaria* spp.;

*Aspergillus* species, such as, for example, *Aspergillus flavus;*

*Cladosporium* species, such as, for example, *Cladosporium cladosporioides;*

*Claviceps* species, such as, for example, *Claviceps purpurea;*

*Fusarium* species, such as, for example, *Fusarium culmorum;*

*Gibberella* species, such as, for example, *Gibberella zeae;*

*Monographella* species, such as, for example, *Monographella nivalis;*

Diseases caused by smut fungi, such as, for example,

*Sphacelotheca* species, such as, for example, *Sphacelotheca reiliana;*

*Tilletia* species, such as, for example, *Tilletia caries;*

*Urocystis* species, such as, for example, *Urocystis occulta;*

*Ustilago* species, such as, for example, *Ustilago nuda;*

Fruit rot caused, for example, by

*Aspergillus* species, such as, for example, *Aspergillus flavus;*

*Botrytis* species, such as, for example, *Botrytis cinerea;*

*Penicillium* species, such as, for example, *Penicillium expansum* or *Penicillium expansum;*

*Rhizopus* species, such as, for example, *Rhizopus stolonifer;*

*Sclerotinia* species, such as, for example, *Sclerotinia sclerotiorum;*

*Verticilium* species, such as, for example, *Verticilium alboatrum;*

Seed- and soil-borne rot and wilt diseases, and also diseases of seedlings, caused, for example, by

*Alternaria* species, such as, for example, *Alternaria brassicicola;*

*Aphanomyces* species, such as, for example, *Aphanomyces euteiches;*

*Ascochyta* species, such as, for example, *Ascochyta lentis;*

*Aspergillus* species, such as, for example, *Aspergillus flavus;*

*Cladosporium* species, such as, for example, *Cladosporium herbarum;*

*Cochliobolus* species, such as, for example, *Cochliobolus sativus* (Conidial form: *Drechslera, Bipolaris* Syn: *Helminthosporium*);

*Colletotrichum* species, such as, for example, *Colletotrichum coccodes;*

*Fusarium* species, such as, for example, *Fusarium culmorum;*

*Gibberella* species, such as, for example, *Gibberella zeae;*

*Macrophomina* species, such as, for example, *Macrophomina phaseolina;*

*Microdochium* species, such as, for example, *Microdochium nivale;*

*Monographella* species, such as, for example, *Monographella nivalis;*

*Penicillium* species, such as, for example, *Penicillium expansum;*

*Phoma* species, such as, for example, *Phoma lingam;*

*Phomopsis* species, such as, for example *Phomopsis sojae;*

*Phytophthora* species, such as, for example, *Phytophthora cactorum;*

*Pyrenophora* species, such as, for example, *Pyrenophora graminea;*

*Pyricuiaria* species, such as, for example, *Pyricularia oryzae;*

*Pythium* species, such as, for example, *Pythium ultimum;*

*Rhizoctonia* species, such as, for example, *Rhizoctonia solani;*

*Rhitopus* species, such as, for example, *Rhizopus oryzae;*

*Sclerotium* species, such as, for example, *Sclerotium rolfsii;*

*Septoria* species, such as, for example, *Septoria nodorum;*

*Typhula* species, such as, for example, *Typhula incarnata;*

*Verticillium* species, such as, for example, *Verticillium dahliae;*

Cancerous diseases, galls and witches' broom caused, for example, by

*Nectria* species, such as, for example, *Nectria galligena;*

Wilt diseases caused, for example, by

*Monilinia* species, such as, for example, *Monilinia laxa;*

Deformations of leaves, flowers and fruits caused, for example, by

*Exobasidium* species, such as, for example, *Exobasidium vexans;*

*Taphrina* species, such as, for example, *Taphrina deformans;*

Degenerative diseases of woody plants caused, for example, by

*Esca* species, such as, for example, *Phaemoniella clamydospora Phaeoacremonium aleophilum* or *Fomitiporia mediterranea;*

*Ganoderma* species, such as, for example, *Ganoderma boninense;*

*Rigndoporus* species, such as, for example, *Rigiduorus lignosus;*

Diseases of flowers and seeds caused, for example, by

*Botrytis* species, such as, for example, *Botrytis cinerea;*

Diseases of plant tubers caused, for example, by

*Rhizoctonia* species, such as, for example, *Rhizoctonia solani;*

*Helminthosporium* species, such as, for example, *Helminthosporium solani;*

Diseases caused by bacteriopathogens, such as, for example,

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

Preference is given to being able to control the following diseases of soya beans:

fungal diseases on leaves, stems, pods and seeds caused, for example, by

*alternaria* leaf spot (*Alternaria* spec. *atrans tenuissima*), anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), dactuliophora leaf spot (*Dactuliophora glycines*), downy mildew (*Peronospora manshurica*), *drechslera* blight (*Drechslera frogeye* leaf spot (*Cercospora sojina*), *leptosphaerulina* leaf spot (*Leptosphaerulina trifolii*), *phyllostica* leaf spot (*Phyllostica sojaecola*), pod and stem blight (*Phomopsis sojae*), powdery mildew (*Microsphaera diffusa*), pyrenochaeta leaf spot (*Pyrenochaea glycines*), *rhizoctonia* aerial, foliage, and web blight (*Rhizoctonia solani*), rust (*Phakopsora pachyrhizi*), scab (*Sphaceloma glycines*), *stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *selerotinia* stem decay (*Sclerotinia sclerotiorum*), *sclerotinia* southern blight (*Sclerotinia rolfsii*), *thielaviopsis* root rot (*Thielaviopsis basicola*).

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application, soil application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seed of plants has been known for a long time and is the subject of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional applications are at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that the particular systemic properties of the compositions according to the invention mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), oilseed rape, peanuts, vegetables (such as tomatoes, cucumbers, onions and lettuce), lawn and ornamental plants. The treatment of the seed of monocotyledonous plants such as cereals (such as wheat, barley, rye and oats), maize and rice and also dicotyledonous plants such as soya beans, potatoes, oilseed rape and cotton is of particular importance.

In the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed used has usually been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the skilled worker and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active compound combinations according to the invention also have a potent strengthening effect in plants. They are therefore suitable for mobilizing the plants' defenses against attack by unwanted microorganisms.

Plant-strengthening (resistance-inducing) compounds are understood as meaning, in the present context, those substances which are capable of stimulating the defense system of plants in such a way that, when subsequently inoculated with unwanted microorganisms, the treated plants display a substantial degree of resistance to these microorganisms.

In the present case, unwanted microorganisms are understood as meaning phytopathogenic fungi, bacteria and viruses. Thus, the compounds according to the invention can be employed for protecting plants against attack by the above-mentioned pathogens within a certain period of time after the treatment.

The period of time over which their protection is effected generally extends from 1 to 300 days, preferably from 1 to 90 days, after the plants have been treated with the active compounds.

The fact that the active compound combinations, at the concentrations required for the controlling of plant diseases, are well tolerated by plants permits a treatment of above-ground plant parts, of propagation stock and seed, and of the soil.

Here, the active compound combinations according to the invention can be used with particularly good results for controlling cereal diseases, such as, for example, against *Puccinia* species, and diseases in viticulture and in the cultivation of fruit and vegetables, such as, for example, against *Botrytis, Venturia* or *Alternaria* species.

The active compound combinations according to the invention are also suitable for increasing the harvest yield. Moreover, they display a low degree of toxicity and are well tolerated by plants.

If appropriate, the active compound combinations according to the invention can also be used in certain concentrations and application rates as herbicides, for influencing plant growth and for controlling animal pests. If appropriate, they can also be employed as intermediates and precursors for the synthesis of further active compounds.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the active compound combinations according to the invention can be employed for protecting industrial materials against attack and destruction by unwanted microorganisms.

In the present context, industrial materials are understood as meaning non-living materials which have been made for use in technology. For example, industrial materials which are to be protected by active compounds according to the invention from microbial modification or destruction can be glues, sizes, paper and board, textiles, leather, wood, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, wood, paints, cooling lubricants and heat-transfer fluids, particularly preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:

*Alternaria* such as *Alternaria tenuis,*
*Aspergillus* such as *Aspergillus niger,*
*Chaetomium* such as *Chaetomium globosum,*
*Coniophora* such as *Coniophora puetana,*
*Lentinus* such as *Lentinus tigrinus,*
*Penicillium* such as *Penicillium glaucum,*
*Polyporus* such as *Polyporus versicolor,*
*Aureobasidium* such as *Aureobasidium pullulans,*
*Sclerophoma* such as *Sclerophoma pityophila,*
*Trichoderma* such as *Trichoderma viride,*
*Escherichia* such as *Escherichia coli,*
*Pseudomonas* such as *Pseudomonas aeruginosa,*
*Staphylococcus* such as *Staphylococcus aureus.*

In addition, the active compound combinations according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided for illustration only.

The active compound combinations can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the active compound combinations according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating soil, the application rates of active compound are generally between 0.1 and 10 000 g/ha, preferably between 1 and 5000 g/ha.

According to the invention, the plants listed can be treated particularly advantageously with the active compound mixtures. The preferred ranges indicated above for the active compounds and mixtures also apply to the treatment of these plants. Particular emphasis is given to the treatment of plants with the compounds or mixtures specifically indicated in the present text.

The active compound combinations according to the invention, in combination with good plant tolerance, favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and also against all or some stages of development. The abovementioned pests include:

Pests from the phylum: *Arthropoda*, in particular from the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of the Anoplura (Phthiraptera), for example, *Damalinia* spp., *Haematopinus* spp., *Linognathus* spp., *Pediculus* spp., *Ptirus pubis, Trichodectes* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anopophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnostema consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderrna* spp., *Liriomyza* spp. *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp, *Stomoxys* spp., *Tabanus* spp., *Tannia* spp., *Tetanops* spp., *Tipula* spp.

From the order of the Heteroptera, for example, *Anasa tristis, Antestiopsis* spp, *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis* cardui, *Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidisirae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaef-*

*bliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of the Isopoda, for example, *Armadillidium vulgare, Oniscus asellus, Porcellio scaber.*

From the order of the Isoptera, for example, *Coptotermes* spp., *Cornitermes cumulans, Ciyptotermes* spp., *Incisitermes* spp., *Microtermes obeli, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella spp, Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella. Kakivoria flavofasciata, Laphygma* spp., *Laspeyresia molesta, Leucinodes orbonalis, Leucoptera* spp., *Lithocolletis* spp. *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Orthoptera, for example, *Acheta dornesticus, Blatta orientalis, Blattella germanica, Dichroplus* spp., *Giyllotalpa* spp., *Leucophaea maderae, Locusta* spp., *Melanoplus* spp., *Periplaneta* spp., *Pulex irritans, Schistocerca gregaria, Supella longipalpa.*

From the order of the Siphonaptera, for example, *Ceratophyllus* spp., *Ctenocephalides* spp., *Tunga penetrans, Xenopsylla cheopis.*

From the order of the Sympliyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Zygentoma (=Thysanura), for example, *Lepisma saccharina, Thermobia domestica.*

Pests from the phylum: Mollusca, in particular from the class of the Bivalvia, for example, *Dreissena* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Animal pests from the phyla: Plathelminthes and Nematoda, in particular from the class of the Helminthes, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

Plant pests from the phylum: Nematoda, i.e. plant-parasitic nematodes, in particular *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

Subphylum: Protozoa

It is furthermore possible to control Protozoa, such as *Eimeria.*

Depending on their particular physical and/or chemical properties, the active compound combinations can be converted into the customary formulations, such as solutions, emulsions, wettable powders, suspensions, powders, foams, dusts, pastes, soluble powders, granules, aerosols, suspoemulsion concentrates, natural and synthetic materials impregnated with active compound, microencapsulations in polymeric substances and in coating materials for seeds, and ULV cool and warm fogging formulations.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates, suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsuiphonates, alkyl sulphates, arylsulphonates, or else protein hydrolysates; suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are, also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 70% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying, oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or a plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl)adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Brvobia* ssp., *Dermanyssus gallinae, Glyciphagus domesticus, Ornithodorus moubat, Rhipicephalus sanguinous, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella gernanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae. Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotornus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla* cheopis.

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humans corporis, Phthirus pubis.*

From the order of the Heteroptera, for example, *Cimex hemipterus, Cimex lectularius, Rhodnius prolixus, Triatoma infestans.*

They are used in aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (genetically modified organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, a more developed root system, a better resistance of the plant species or plant variety, increased offshoot growth, higher plant vitality, increased tolerance to high or low temperatures, increased tolerance to drought or to water or soil salt content, increased flowering performance, easier harvesting, accelerated maturation, higher harvest yields, bigger fruits, greater plant size, greener leaf colour, earlier blooming, better quality and/or a higher nutritional value of the harvested products, higher sugar concentration in the fruits, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized in particular are increased defense of the plants against insects, by toxins formed in the plants, in particular those formed in the plants by the genetic material from *Bacillus thuringiensis*. (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed may particularly advantageously, according to the invention, be treated with the active compound mixtures according to the invention. The preference ranges given above for the mixtures also apply to the treatment of these plants. Particular emphasis is given to the treatment of plants with the mixtures listed specifically in the current text.

The good insecticidal, acaricidal and fungicidal action of the active compound combinations according to the invention is demonstrated by the examples below. While the individual active compounds show weaknesses in their action, the combinations show an action which exceeds a simple sum of actions.

A synergistic effect is always present in the insecticides, acaricides and fungicides when the insecticidal or fungicidal action of the active compound combinations exceeds the total of the action of the active compounds when applied individually.

The expected insecticidal, acaricidal or fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy or kill rate, expressed in % of the untreated control, when employing active compound A at an application rate of m g/ha or in a concentration of m ppm, Y is the efficacy or kill rate, expressed in % of the untreated control, when employing active compound B at an application rate of n g/ha or in a concentration of n ppm and E is the efficacy or kill rate, expressed in % of the untreated control, when employing active compounds A and B at application rates of m and n g/ha or in a concentration of m and n ppm, then $$E = X + Y - \frac{X \cdot Y}{100}$$

Here, 0% means an efficacy or kill rate which corresponds to that of the control, whereas an efficacy or kill rate of 100% means that no infection is observed.

If the actual insecticidal, acaricidal or fungicidal kill rate or efficacy exceeds the calculated value, the killing action of the combination is superadditive, i.e. a synergistic effect is present. In this case, the actually observed kill rate must exceed the value calculated using the above formula for the expected kill rate (E).

The invention is illustrated by the examples below:

EXAMPLES

Example 1

*Rhizoctonia solani* Test (in vitro)/Microtitre Plates

The microtest is carried out in microtitre plates using Potato Dextrose Broth (PDB) as liquid test medium. The active compounds are used as technical-grade a.i., dissolved in acetone. For inoculation, a mycelium suspension of *Rhizoctonia solani* is used. After 7 days of incubation in the dark and with shaking (10 Hz), the transparency in each filled cavity of the microtitre plates is determined with the aid of a spectrophotometer.

Here, 0% means an efficacy which corresponds to the growth in the controls, whereas an efficacy of 100% means that no fungal growth is observed.

The table below clearly shows that the activity found for the active compound combination according to the invention is greater than the calculated activity, i.e. that a synergistic effect is present.

TABLE

*Rhizoctonia solani* test (in vitro)/microtest

| Active compound Known: | Application rate of active compound in ppm | % efficacy |
|---|---|---|
| penflufen | 0.3 | 20 |
| sulfoxaflor | 0.3 | 0 |

Mixture according to the invention:

| | Mixing ratio | Application rate of active compound in ppm | Actual efficacy | Expected value calculated using Colby's formula |
|---|---|---|---|---|
| penflufen + sulfoxaflor | 1:1 | 0.3 + 0.3 | 43 | 20 |

Example 2

*Pyrenophora teres* Test (in vitro)/Microtitre Plates

The microtest is carried out in microtitre plates using Potato Dextrose Broth (PDB) as liquid test medium. The active compounds are used as technical-grade a.i., dissolved in methanol. For inoculation, a spore suspension of *Pyrenophora teres* is used. After 5 days of incubation in the dark and with shaking (10 Hz), the transparency in each filled cavity of the microtitre plates is determined with the aid of a spectrophotometer.

Here. 0% means an efficacy which corresponds to the growth in the controls, whereas an efficacy of 100% means that no fungal growth is observed.

The table below clearly shows that the activity found for the active compound combination according to the invention is greater than the calculated activity, i.e. that a synergistic effect is present.

TABLE

*Pyrenophora teres* test (in vitro)/microtest

| Active compound Known: | Application rate of active compound in ppm | % efficacy |
|---|---|---|
| penflufen | 1 | 26 |
| Rynaxypyr (chlorantraniliprole) | 1 | 11 |

Mixture according to the invention:

| | Mixing ratio | Application rate of active compound in ppm | Actual efficacy | Expected value calculated using Colby's formula |
|---|---|---|---|---|
| penflufen + Rynaxypyr | 1:1 | 1 + 1 | 49 | 34 |

Example 3

*Phaedon cochleariae* Larvae Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being sprayed with the active compound preparation of the desired concentration and are populated with larvae of the mustard beetle (*Phaedon cochleariae*) while the leaves are still moist.

After the desired period of time, the kill rate in % is determined. Here, 100% means that all beetle larvae have been killed; 0% means that none of the beetle larvae have been killed. The kill rates determined are calculated using Colby's formula.

In this test, the following active compound combination in accordance with the present application shows a synergistically enhanced activity compared to the active compounds applied individually:

TABLE 1

Phaedon cochleariae larvae test

| Active compound | Concentration ppm | Kill in % after 1 d | |
|---|---|---|---|
| penflufen | 500 | 0 | |
| sulfoxaflor | 100 | 25 | |
| penflufen + sulfoxaflor (5:1) | 500 + 100 | found* | calc.** |
| according to the invention | | 60 | 25 |
| **Active compound** | **Concentration ppm** | **Kill in % after 3 d** | |
| penflufen | 200 | 0 | |
| Rynaxypyr | 4 | 80 | |
| penflufen + Rynaxypyr (50:1) | 200 + 4 | found* | calc.** |
| according to the invention | | 95 | 80 |

*found = activity found

**calc. = activity calculated using Colby's formula

The invention claimed is:

1. A composition comprising (1) penflufen of the formula N-[2-(1,3-dimethylbutyl)phenyl]-5-fluoro-1,3-dimethyl-1H-pyrazole-4-carboxamide:

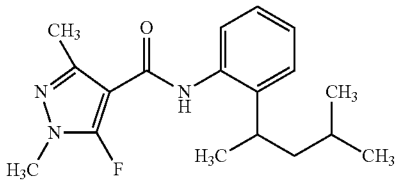 [SMILES: Cc1nn(C)c(F)c1C(=O)Nc1ccccc1C(C)CC(C)C]

and (2) Rynaxypyr of the formula 3-bromo-N-[4-chloro-2-methyl-6-(methylcarbamoyl)phenyl]-1-(3-chloropyridin-2-yl)-1H-pyrazole-5-carboxamide:

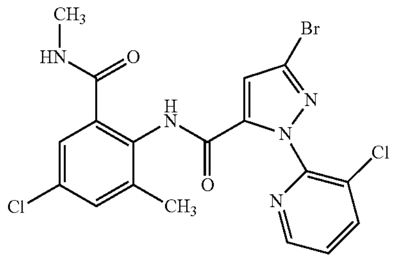 [SMILES: CNC(=O)c1cc(Cl)cc(C)c1NC(=O)c1cc(Br)nn1-c1ncccc1Cl]

wherein said penflufen and Rynaxypyr are present in a weight ratio of from 50:1 to 1:50.

2. A method for controlling unwanted insects, acarids or phytopathogenic fungi, comprising allowing the composition according to claim 1 to act on said unwanted insects or acarids, and/or a habitat thereof, and/or said unwanted phytopathogenic fungi, and/or a habitat thereof.

3. The method according to claim 2 wherein the habitat is a plant.

4. The method according to claim 3 wherein the plant is a tansgenic plant.

5. A method for controlling unwanted insects, acarids or phytopathogenic fungi, comprising applying the composition according to claim 1 to the unwanted insects, acarids or phytopathogenic fungi, and/or their habitat, and/or to the seed of a plant.

6. The composition according to claim 1 which is a synergistically effective composition.

7. The composition according to claim 1 further comprising surfactants and/or extenders.

8. A process for preparing a pesticidal composition comprising mixing the composition according to claim 1 with surfactants and/or extenders.

9. A method of treating seed comprising applying the composition according to claim 1 to said seed.

10. The method according to claim 9 wherein said seed is seed of a transgenic plant.

11. The composition according to claim 1 further comprising seed.

* * * * *